United States Patent
Terasawa et al.

(10) Patent No.: US 8,488,866 B2
(45) Date of Patent: Jul. 16, 2013

(54) METHOD OF INSPECTING MASK PATTERN AND MASK PATTERN INSPECTION APPARATUS

(75) Inventors: Tsuneo Terasawa, Tokyo (JP); Toshihiko Tanaka, Tokyo (JP); Hiroyuki Shigemura, Kanagawa (JP); Hajime Aoyama, Tokyo (JP); Osamu Suga, Tokyo (JP)

(73) Assignees: Renesas Electronics Corporation, Kanagawa (JP); Fujitsu Semiconductor Limited, Kanagawa (JP)

( * ) Notice: Subject to any disclaimer, the term of this patent is extended or adjusted under 35 U.S.C. 154(b) by 612 days.

(21) Appl. No.: 12/708,041

(22) Filed: Feb. 18, 2010

(65) Prior Publication Data

US 2010/0208978 A1   Aug. 19, 2010

(30) Foreign Application Priority Data

Feb. 18, 2009 (JP) ................................. 2009-034729

(51) Int. Cl.
*G06K 9/00* (2006.01)
(52) U.S. Cl.
USPC ......................................... 382/144; 382/141
(58) Field of Classification Search
USPC ................ 382/100, 141, 144–151, 140, 154, 382/218; 356/237.1–237.6, 388–395
See application file for complete search history.

(56) References Cited

U.S. PATENT DOCUMENTS

| 5,502,306 | A | 3/1996 | Meisburger et al. |
| 7,894,051 | B2 | 2/2011 | Hirano et al. |
| 2005/0031974 | A1* | 2/2005 | Fukuhara ........................ 430/30 |
| 2006/0018530 | A1* | 1/2006 | Oaki et al. ..................... 382/144 |
| 2006/0222233 | A1* | 10/2006 | Sugihara et al. .............. 382/144 |
| 2008/0268352 | A1 | 10/2008 | Takai |

FOREIGN PATENT DOCUMENTS

| JP | 10-282008 | 10/1998 |
| JP | 2003-172710 | 6/2003 |
| JP | 2003-202307 | 7/2003 |
| JP | 2004-061289 | 2/2004 |
| JP | 2004-077390 | 3/2004 |
| JP | 2004-212221 | 7/2004 |
| JP | 2007-011169 | 1/2007 |
| JP | 2008-268424 | 11/2008 |
| JP | 2008-277541 | 11/2008 |

OTHER PUBLICATIONS

JP Office Action dated Feb. 19, 2013, with English translation; Application No. 2009-034729.

* cited by examiner

*Primary Examiner* — Tri T Ton
(74) *Attorney, Agent, or Firm* — Young & Thompson

(57) ABSTRACT

A inspection image data of the chip A is captured and the data representing the amount of correction of flare corresponded to the chip A is appropriately loaded from the map storage block. Next, a inspection image of the chip A' is captured, and the data representing the amount of correction of flare corresponded to the chip A' is loaded from the flare map storage block as the amount of shifting of the edge of the contour of the pattern. The amount of correction is converted, by a correction data generation block which is a correction data generator, into the amount of geometrical correction of pattern which provides correction data. In the comparison block, the images of the geometry of two chips are compared and corrected on the amount of correction of flare generated by a correction data generation block, to thereby judge whether defect is found or not.

16 Claims, 15 Drawing Sheets

METHOD OF INSPECTING MASK PATTERN AND MASK PATTERN INSPECTION APPARATUS

This application is based on Japanese patent application No. 2009-034729 the content of which is incorporated hereinto by reference.

BACKGROUND

1. Technical Field

The present invention relates to a method of inspecting mask pattern and a mask pattern inspection apparatus, and in particular to a method and an apparatus useful for inspecting pattern defect on a mask which is configured by a multi-layered-film mask substrate which reflects EUV (Extreme Ultra Violet) light, and a finely-patterned material layer formed thereon using a material which absorbs the EUV light.

2. Related Art

Semiconductor devices (semiconductor integrated circuit devices) are manufactured on a mass scale by repetitively using a photolithographic process, in which a mask, or a plate having a circuit pattern, is illuminated by light, so as to project the circuit pattern through a reduction optics onto a semiconductor substrate (referred to as "wafer", hereinafter).

Keeping pace with recent advances in shrinkage of the semiconductor devices, investigations have been made on increase in resolution by further shortening wavelength of photo-lithography. In place of conventionally developed ArF lithography which makes use of argon fluoride (ArF) excimer laser light at 193 nm, EUVL (Extreme Ultra Violet Lithography) at a far shorter wavelength of 13.5 nm has been under development.

Since transmissive masks are of no use in this wavelength range due to absorbance of light by the constitutive materials, so that multi-layered-film reflective substrates, which make use of reflection (Bragg reflection) on multi-layered films typically composed of molybdenum (Mo) and silicon (Si), are used as mask blanks for EUVL.

Multi-layered film reflection may be understood as reflection making use of a sort of interference. The mask for EUVL is configured by a multi-layered-film blank which is composed of a quartz glass substrate or low-thermal-expansion glass substrate, and a multi-layered film typically composed of Mo and Si formed thereon, and an absorber pattern formed on the blank.

In the process of transfer of the absorber pattern onto a semiconductor wafer, any defect in the absorber pattern is causative of defect in the semiconductor integrated circuit, so that the absorber pattern needs defect inspection before the mask is supplied. Die-to-die comparison method, illustrated in FIG. 14, is a conventionally known method of inspecting mask defect, in which two chips (chips A, A') 70, 71 having the same pattern are respectively observed in a scanning mode using a sensor having a plurality of pixels, the obtained chip images are compared, and any difference therebetween is detected using an appropriate defect detection algorithm (see Japanese Published patent application A-H10-282008, Japanese Laid-open patent publication 2004-212221, 2004-61289 and 2004-77390, for example).

In view of efficient capture of chip images, it is preferable to scan, en bloc, over a plurality of dies which are aligned in sequence in the longitudinal direction of a stripe-form area (stripe) 72. For this purpose, a method generally adopted is such as sequentially capturing the images, storing the captured images into a memory, and comparing the images in the memory concomitantly with the storage operation, or upon completion of the storage operation for a single stripe.

Another known method is die-to-database comparison method, in which a design data used for designing the geometry of the absorber pattern is read, the read data is subjected to an appropriate filtering operation, and then compared with a chip image to thereby detect any difference therebetween.

The filtering operation is aimed at degrading the design data while considering degradation in an actually-obtainable inspection image ascribable to manufacturing processes, resolution characteristics of the inspection optics, characteristics of the sensor and so forth, so as to match it to the actually-obtainable inspection image.

As a method of inspecting defect of the filmy mask pattern, there has been known another method of precisely detecting defect, by appropriately correcting a drawing pattern data to thereby generate a pattern inspection data, so as to avoid difference between the pattern inspection data and an image data obtainable by a pattern defect inspection apparatus, and then by comparing the pattern inspection data and the image data (see Japanese Laid-open patent publication NO. 2007-11169).

FIG. 12A illustrates an exemplary EUVL mask M1, under development by the present inventors, as viewed from the patterned surface. The mask M1 has a device pattern area MDE which represents a semiconductor integrated circuit pattern located at the center thereof, and alignment mark areas MA1, MA2, MA3, MA4 which typically contain mask alignment marks and wafer alignment marks located in the peripheral area.

FIG. 12B is a drawing illustrating an exemplary section of the EUVL mask M1, taken at the device pattern area MDE. It is seen that a multi-layered film 52 described in the above is provided on a substrate 51 which is composed of quartz glass, low-thermal-expansion material or the like, and a capping layer 53 is provided thereon. Further thereon, an absorber pattern 55 is provided, while placing a buffer layer 54 in between. On the other hand, on the back surface of the substrate 51, there is provided a metal film 56 coated thereon, for the convenience of electrostatic chucking of the mask.

FIG. 13 is a drawing illustrating a system used for reduction projection of a pattern on the EUVL mask M1, making use of an EUV projection exposure apparatus. EUV light having a center wavelength of 13.5 nm, emitted from a light source 61, propagates through an illumination optics 62 configured by multi-layered-film reflection mirrors, and illuminates the patterned surface of the EUVL mask M1 pattern.

Reflected light on the patterned surface then propagates through a reduction projection optics 63 composed of multi-layered-film reflection mirrors, and projects the mask pattern onto a semiconductor wafer 64. The semiconductor wafer 64 is placed on a stage 65, so as to allow a large number of patterns to be transferred onto desired areas on the semiconductor wafer 64, by repeating movement of the stage 65 and the pattern transfer.

The present inventors, however, found out a problem in the above-described technique of inspecting pattern defect in the EUVL mask used for the EUV projection exposure apparatus.

In the EUV lithographic apparatus, scattered stray light (flare) ascribable to surface roughness of the mirrors composing the projection optics tends to increase, so that even portions of the pattern, expected to be darkened, may adversely be affected by the flare in the process of demagnifying transfer of the pattern on the EUVL mask M1 onto the semiconductor wafer.

As a consequence, the line width of a projected image may vary if the periphery of the pattern is bright. Since the total amount of scattered light increases inversely proportional to the square of wavelength, so that the amount of flare in EUVL, making use of light at a wavelength shorter by one order of magnitude than that in the conventional photo-lithography, increases by two orders of magnitude or more.

Moreover, influences of the flare may vary depending on to what degree the bright portion occupies the area within a micrometer- or millimeter-order range around a target pattern.

Accordingly, on the EUVL mask, even the same geometrical patterns on the design basis including the adjacent patterns need be applied with different flare correction patterns, depending on positions of the chips containing such patterns. In optical proximity correction (OPC) adopted in the conventional photo-lithography, it has been good enough if only the same correction pattern is adopted to the same geometrical patterns including the adjacent patterns.

In contrast, EUVL is different from the conventional OPC in that even the same geometrical patterns including the adjacent patterns need different flare correction, depending on the pattern density in the range as small as the chip size.

As a consequence, as illustrated in FIGS. 15A and 15B, an absorber pattern 73 contained in chip A and an absorber pattern 72 contained in chip A' have different dimensions on the mask, even if they have the same geometrical patterns on the design basis. For this reason, the conventional die-to-die comparison method suffers from a problem of inaccurate inspection.

On the other hand, the die-to-database method may successfully avoid a problem of degraded inspection accuracy ascribable to the different dimension as described in the above. The filtering operation described in the above, however, needs a huge volume of calculation, making it difficult to achieve satisfactory levels of accuracy and rapidness in the inspection at the same time.

SUMMARY

According to the present invention, there is provided a method of inspecting a mask pattern for judging presence of pattern defect in a plurality of chip patterns formed on an EUV lithographic mask. The method includes:

acquiring a referential measurement pattern by irradiating light or electron beam to a referential chip pattern contained in a referential inspection area, which is selected as a reference for comparison out of the plurality of chip patterns, and by capturing reflected light, secondary electron or reflected electron from the referential inspection area using an imaging unit;

acquiring a comparative measurement pattern by irradiating light or electron beam to a comparative chip pattern contained in a comparative inspection area, which is selected from the plurality of chip patterns but other than the referential chip pattern, and by capturing reflected light, secondary electron or reflected electron from the comparative inspection area using an imaging unit;

correcting the referential measurement pattern and the comparative measurement pattern, based on a first correction data for correcting the referential measurement pattern and/or a second correction data for correcting the comparative measurement pattern, loaded from elsewhere; and judging presence of pattern defect by comparing the thus-corrected referential measurement pattern and the thus-corrected comparative measurement pattern.

According to the present invention, there is also provided a mask pattern inspection apparatus for judging presence of pattern defect in a plurality of chip patterns formed on an EUV lithographic mask. The apparatus includes:

a pattern detection block which respectively acquires a referential measurement pattern and a comparative measurement pattern, by detecting reflected light, secondary electron or reflected electron respectively from an arbitrary inspection area in a referential chip pattern, and in a comparative chip pattern other than the referential chip pattern, out of the plurality of chip patterns;

a position detection block which respectively detects positions of the thus-detected referential measurement pattern and the thus-detected comparative measurement pattern;

a flare map storage block which stores flare correction data used for correcting influence of flare possibly generated in EUV lithography for each area in a mask pattern; and a comparison block which judges presence of pattern defect, by acquiring a first flare correction data which corresponds to the position of the referential measurement pattern, and a second flare correction data which corresponds to the position of the comparative measurement pattern from the flare map storage block, by correcting the referential measurement pattern using the first flare correction data, by correcting the comparative measurement pattern using the second flare correction data, and by comparing the thus-corrected referential measurement pattern and the thus-corrected comparative measurement pattern.

Other aspects of the present invention will be briefed below.

In the present invention, an amount of correction to be adopted to a mask pattern data is preliminarily extracted, and a flare map data which stores the amount of correction as information specific to each area in the mask pattern, is preliminarily prepared. Similarly to as in the conventional die-to-die comparison method, an inspection image of a first chip is captured, and stored into a memory. At the same time, the amount of correction of flare corresponded to a first chip area is loaded. Next, an inspection image of a second chip is captured, and compared with the inspection image of the first chip. In this process, also the amount of correction of flare corresponded to the second chip area is loaded, and comparative calculation taking the difference in the amount of correction of flare into consideration is carried out. Defect is recognized if any difference is found as a result of comparison.

Other possible methods of comparative calculation, taking the difference in the amount of correction of flare into consideration, include a method of examining whether difference between the inspection image of the first chip and the inspection image of the second chip is equivalent to difference between the amounts of correction of flare, and a method of comparing inspection images of the individual chips, after being corrected by respectively subtracting their specific amounts of correction of flare.

Although data of semiconductor integrated circuit pattern formed on a mask generally have a hierarchical structure, the flare correction data herein does not always necessarily have a hierarchical structure, and may have a flat expansion structure.

Effects expectable from representative aspects of the present invention disclosed in this specification will be briefed as below:

(1) Patterns on EUV lithographic masks may be inspected based on a method similar to the die-to-die comparison method.

(2) By virtue of the effect (1) in the above, pattern defect in the EUV lithographic masks may be inspected in highly precise and rapid manners.

BRIEF DESCRIPTION OF THE DRAWINGS

The above and other objects, advantages and features of the present invention will be more apparent from the following description of certain preferred embodiments taken in conjunction with the accompanying drawings, in which.

DETAILED DESCRIPTION OF PREFERED EMBODIMENT

The invention will now be described herein with reference to illustrative embodiments. Those skilled in the art will recognize that many alternative embodiments can be accomplished using the teachings of the present invention and that the invention is not limited to the embodiments illustrated for explanatory purposes.

Embodiments of the present invention will be detailed below, referring to the attached drawings. Note that any similar constituent in all drawings will be given a similar numeral or symbol in principle, and explanation therefor will not be repeated.

First Embodiment

Figure 1:
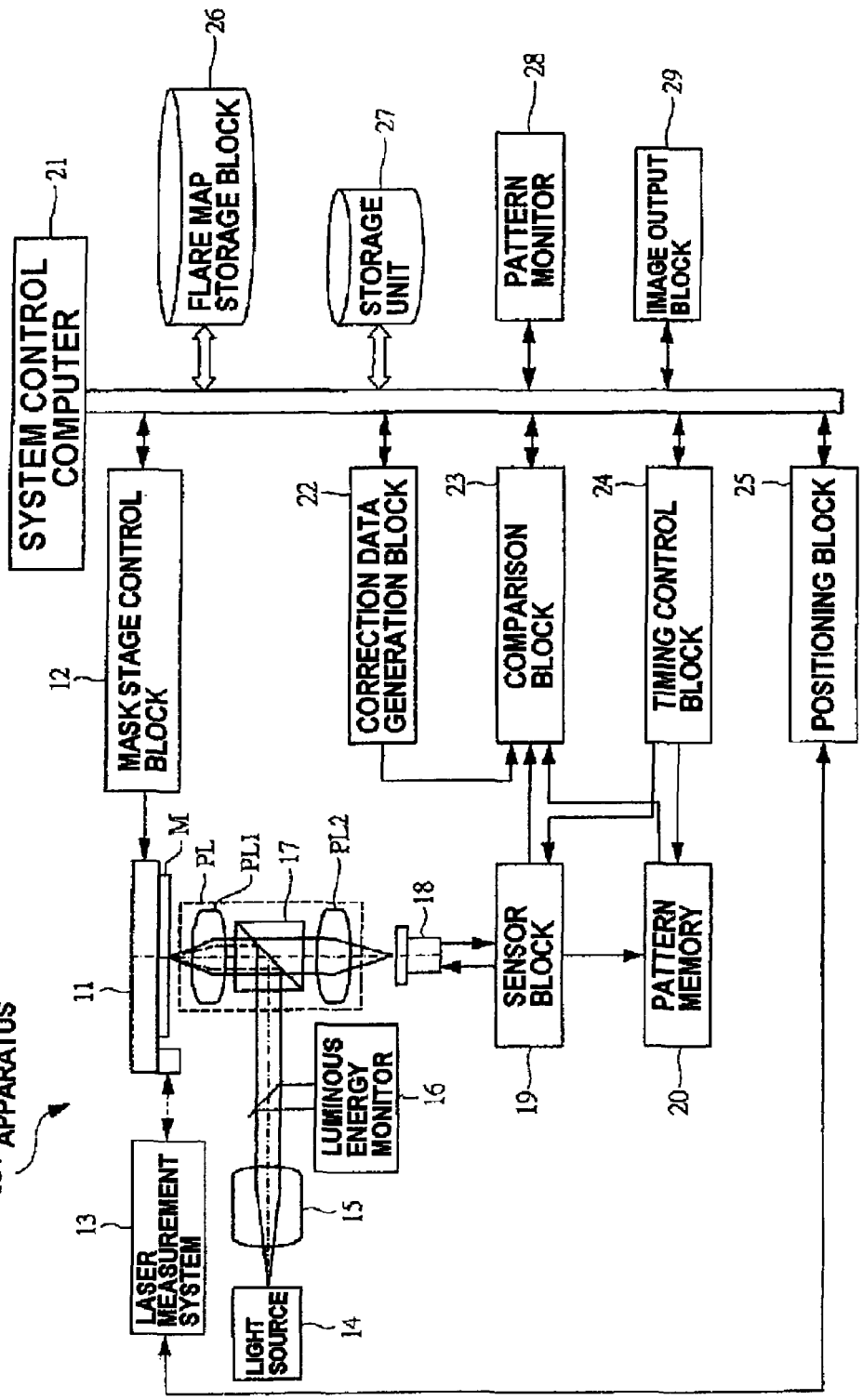
FIG. 1 is an explanatory drawing illustrating an exemplary configuration of a mask pattern defect inspection apparatus according to a first embodiment of the present invention.
Figure 2:
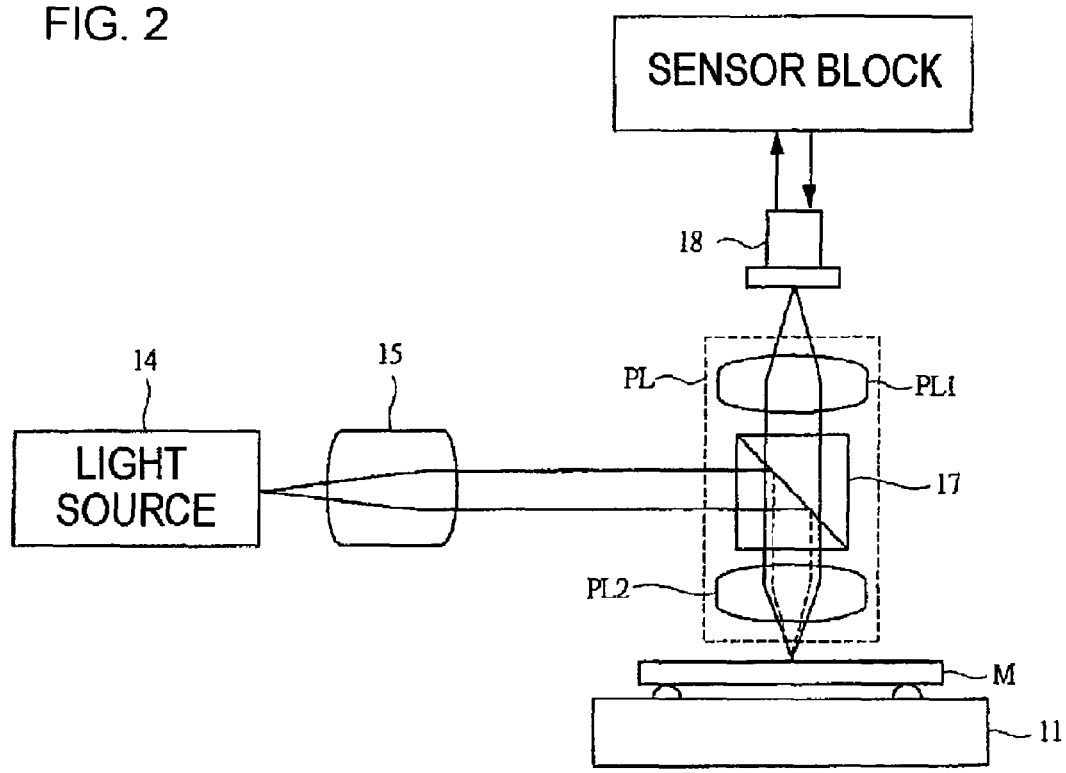
FIG. 2 is an explanatory drawing extractively illustrating an exemplary configuration of a mask pattern defect inspection apparatus according to one embodiment of the present invention, similarly configured except for the inspection optics.
Figure 3A:
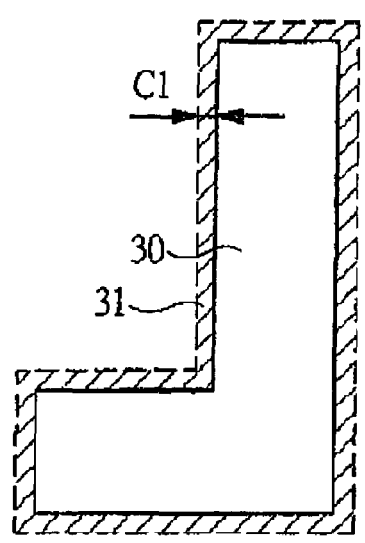
FIGS. 3A and 3B are explanatory drawings illustrating two exemplary mask patterns having the same geometrical pattern but applied with different correction data to give different dimensions, in a first embodiment.
Figure 3B:
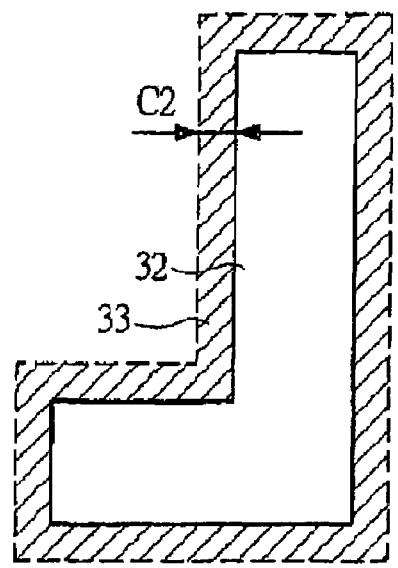
Figure 4:
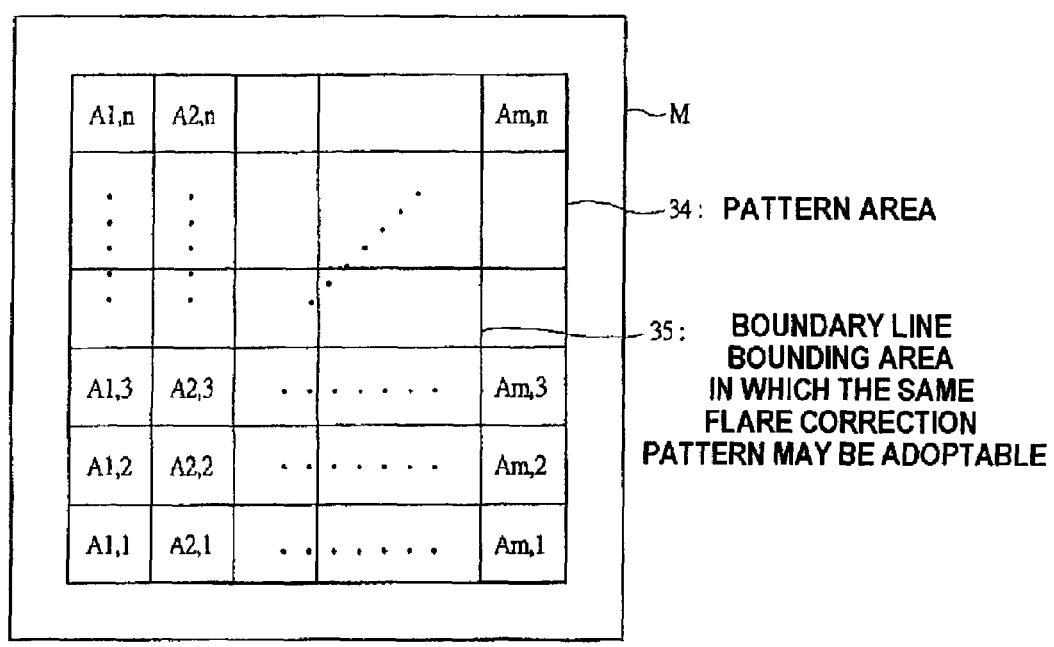
FIG. 4 is an explanatory drawing illustrating an exemplary correction data map used for the mask pattern defect inspection apparatus illustrated in FIG. 1, according to which correction data are applied depending on areas on a mask.
Figure 5:
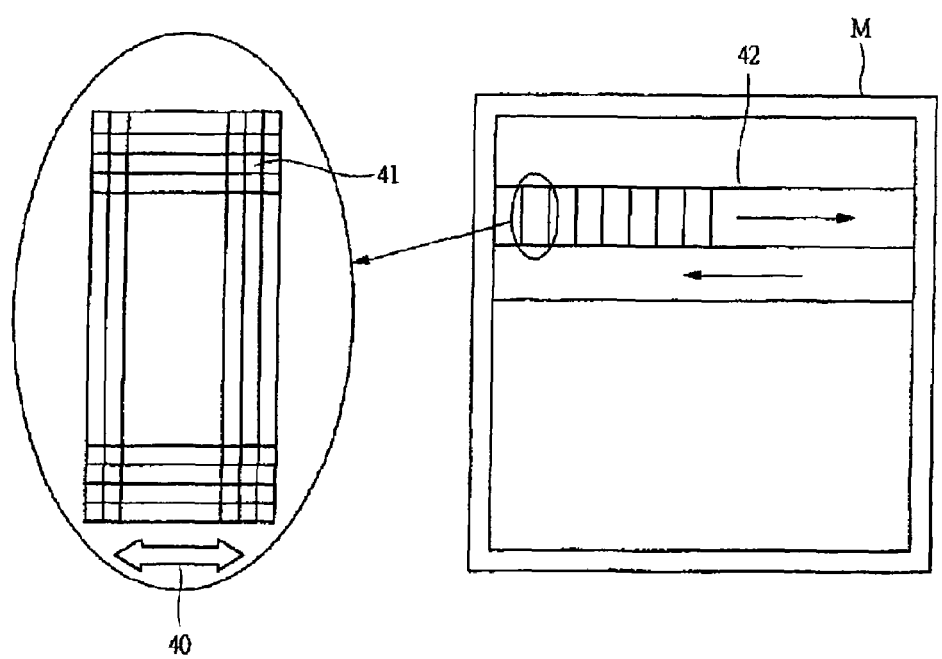
FIG. 5 is an explanatory drawing illustrating an inspection stripe on a multi-layered-film mask and pixels of an inspection sensor.
Figure 6:
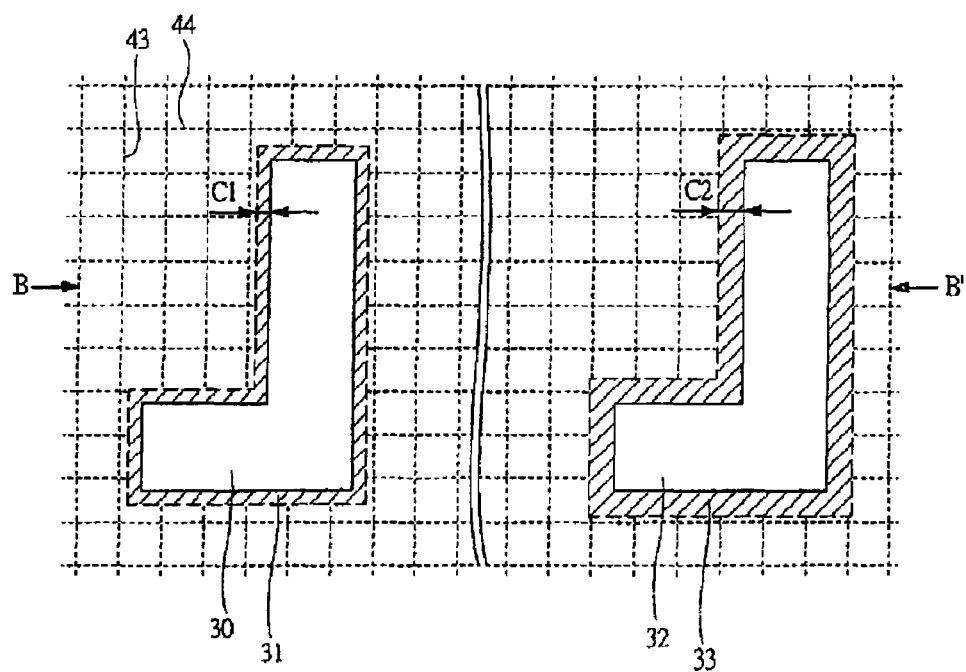
FIG. 6 is an explanatory drawing illustrating relations between patterns in chip areas and pixels of captured images in the process of capturing images.
Figure 7A:
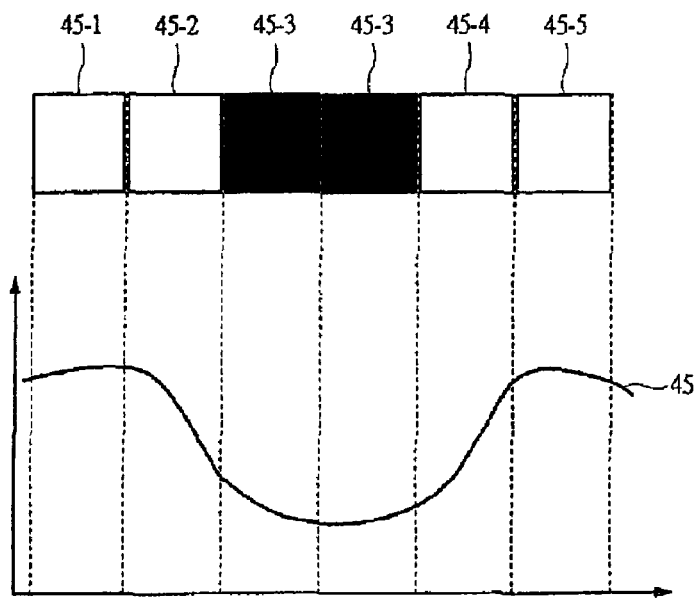
FIGS. 7A and 7B are explanatory drawings illustrating intensity distribution of an inspection image captured into a pixel array of a sensor aligned in a single row, and intensity distribution of an inspection image focused on a sensor surface.
Figure 7B:
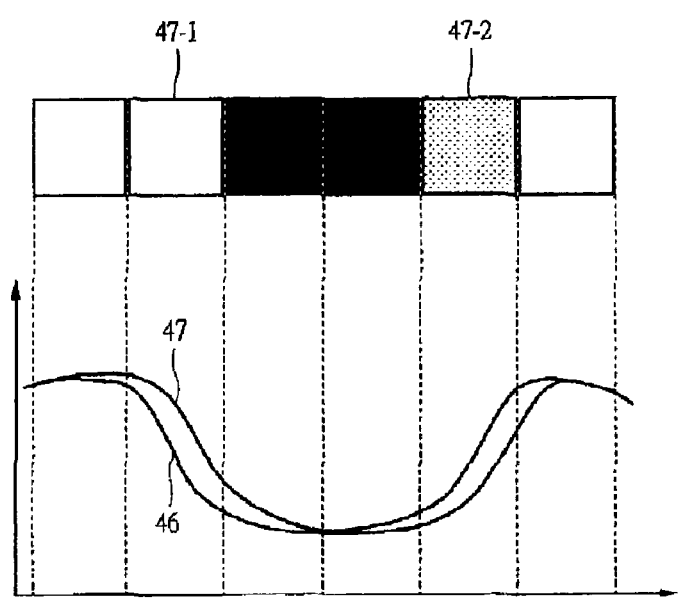
Figure 8:
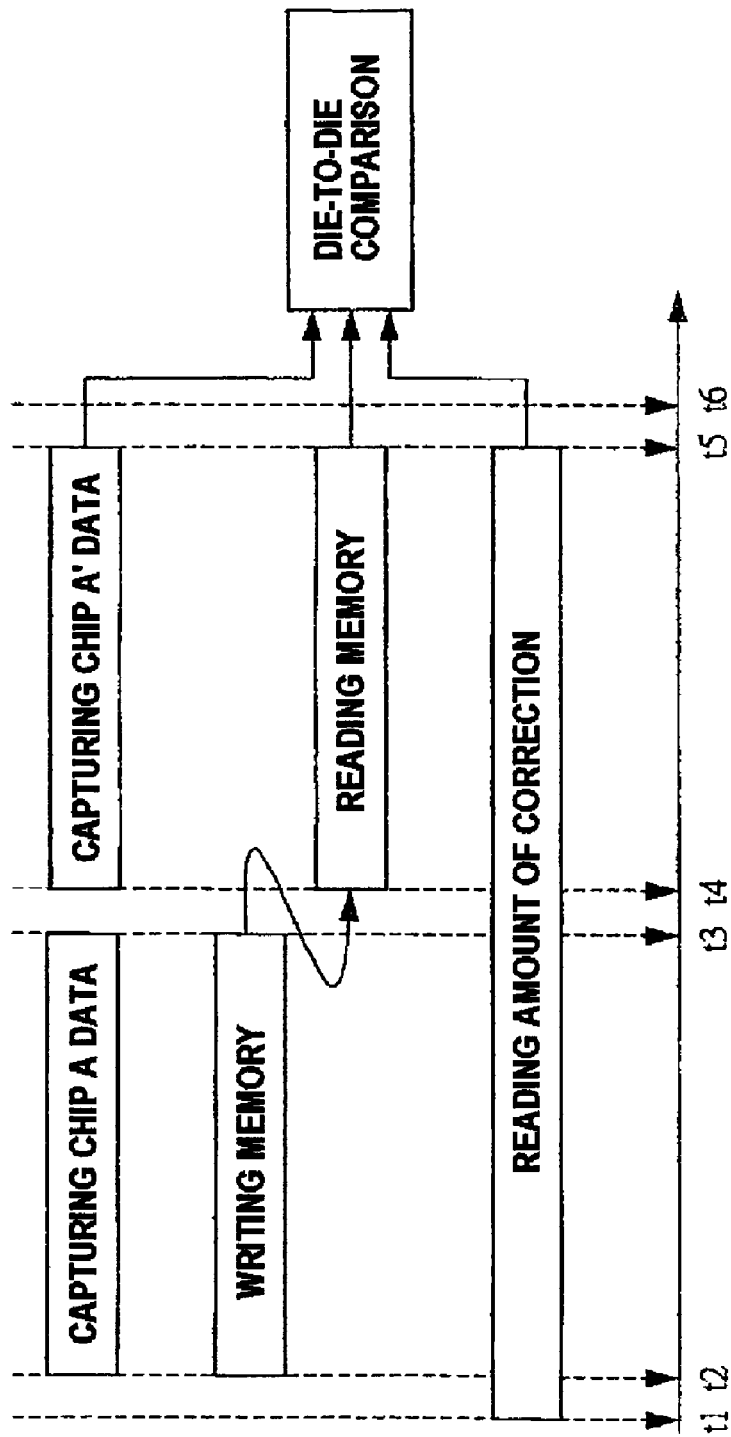
FIG. 8 is a time chart illustrating processing procedures of the inspection images corresponded to a single inspection stripe in the mask pattern defect inspection apparatus illustrated in FIG. 1.
Figure 9:
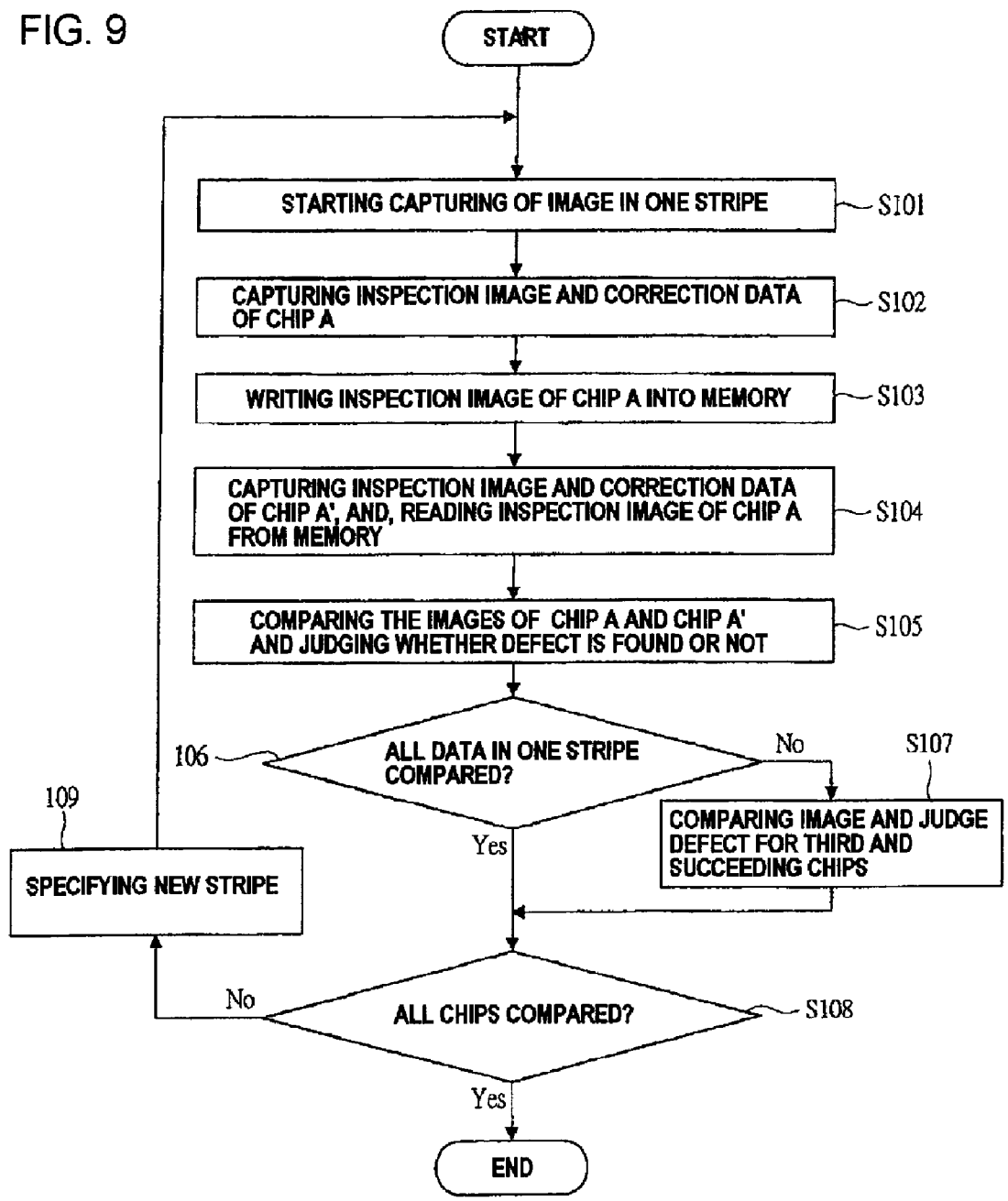
FIG. 9 is a flow chart illustrating a flow of processing of the mask defect inspection in the mask pattern defect inspection apparatus illustrated in FIG. 1.

FIG. 1 is a drawing illustrating an exemplary configuration of a mask pattern defect inspection apparatus according to a first embodiment of the present invention; FIG. 2 is a drawing illustrating another exemplary configuration of a mask pattern defect inspection apparatus similarly configured except for the inspection optics; FIGS. 3A and 3B are drawings illustrating two exemplary mask patterns having the same geometrical pattern but applied with different correction data to give different dimensions, in the first embodiment; FIG. 4 is a drawing illustrating an exemplary correction data map used for the mask pattern defect inspection apparatus illustrated in FIG. 1, according to which correction data are applied depending on areas on a mask; FIG. 5 is a drawing illustrating an inspection stripe on a multi-layered-film mask and pixels of an inspection sensor; FIG. 6 is a drawing illustrating relations between patterns in chip areas and pixels of captured images in the process of capturing images; FIGS. 7A and 7B are drawings illustrating intensity distribution of an inspection image captured into a pixel array of a sensor aligned in a single row, and intensity distribution of an inspection image focused on a sensor surface; FIG. 8 is a time chart illustrating processing procedures of the inspection images corresponded to a single inspection stripe in the mask pattern defect inspection apparatus illustrated in FIG. 1; and FIG. 9 is a flow chart illustrating a flow of inspection of mask defect which takes place in the mask pattern defect inspection apparatus illustrated in FIG. 1.

In the first embodiment, as illustrated in FIG. 1, a mask pattern inspection apparatus 10 has a mask stage 11. A multi-layered-film mask M is fixed to the mask stage 11. The multi-layered-film mask M is a multi-layered film adoptable to EUV exposure, typically composed of molybdenum (Mo) and silicon (Si). The mask stage 11 is moved by a mask stage control block 12 respectively in the X-, Y- and O-directions.

Methods of fixing the multi-layered-film mask M include a method of supporting the side faces of the mask, and a method of using electro-static chucking on the back surface. Position of the multi-layered-film mask M, or consequently position of the mask stage 11, is detected by a laser measurement system 13, and sent to a positioning block 25 described later.

On the other hand, inspection light emitted from a light source 14 is allowed to pass through an illumination optics 15 and a beam splitter 17, and irradiated on a pattern of the multi-layered-film mask M. The inspection light adoptable herein is DUV (deep ultraviolet radiation) having a wavelength typically ranging from 190 nm or around to 270 nm or around.

Reflected light from the multi-layered-film mask M is allowed to pass through the beam splitter 17, and a magnification imaging optics PL which contains lenses PL1, PL2, and then irradiated on the light-receiving surface of a sensor 18 to give a magnified image of the pattern. The sensor 18 configures a detection block. The magnified image is divided into strip-like inspection areas each having a width of as narrow as 150 µm to 250 µm or around. A system control computer 21 moves the mask stage 11 so that the inspection areas may continuously be scanned, to thereby proceed inspection. Luminous energy of the inspection light is constantly, or occasionally measured using a luminous energy monitor 16.

The magnified image of the pattern formed on the light-receiving surface of the sensor 18 is subjected to photoelectric conversion, and is further subjected to A/D (analog/digital) conversion by a sensor block 19 which configures the detection block. In this way, image data expressing a pattern image is produced.

The image data is sent, together with position information of the mask stage 11 output from the positioning block 25, to a pattern memory 20, or to a comparison block 23 which configures a comparator. Timing of output of image data from the sensor block 19 is controlled by a scanning control signal which is output from a timing control block 24. The pattern memory 20 has a capacity sufficient for storing image pattern data over the full length of the strip-like inspection area.

The pattern memory 20 is configured to concomitantly proceed read operation of already-stored image pattern data, and write operation of newly-stored image pattern data.

The amount of correction of flare is determined for each of a plurality of sub-areas produced by dividing the mask pattern. The amount of correction of flare is stored into a flare map storage block 26 prior to execution of the mask inspection. As described later, the amount of correction is converted, by a correction data generation block 22 which is a correction data generator, into the amount of geometrical correction of pattern which provides correction data, and is then sent to the comparison block 23. Note that a single mask pattern generally has a plurality of identical chip patterns, whereas the sub-areas are formed by dividing each chip pattern into portions having the same geometry.

The amount of correction of flare may be generated, in the process of designing the mask pattern, by a simulation based on layout and density (contrast) of pattern. The amount of correction of flare specifically represents the amount of shifting of an edge which determines the contour of the pattern.

The amount of correction of flare, which is determined herein for every mask pattern, may alternatively be determined for every combination of the mask pattern and a light exposure apparatus, for the case where mode of generation of flare is different from apparatus to apparatus.

In the drawing, reference numeral 21 represents a system control computer for controlling the entire portion of the inspection apparatus, 27 represents a storage unit for storing various data and results of inspection, 28 represents a pattern monitor, and 29 represents an image output block.

The multi-layered-film mask M, illustrated in FIG. 1 so as to be fixed by the electro-static chucks on the mask stage 11, with the patterned surface thereof faced down, may alternatively be placed on the top surface of the mask stage 11, with the patterned surface thereof faced up, as illustrated in FIG. 2.

In this case, the multi-layered-film mask M may be fixed onto the mask stage 11, or may simply be placed on the mask 11 by three-point supporting. Inspection light to be irradiated on the multi-layered-film mask M comes from the upper side of the multi-layered-film mask M, and the reflected light propagates through the magnification imaging optics PL to be focused on the sensor 18 to give a magnified image. Data handling thereafter, and configuration of the inspection apparatus are equivalent to those illustrated in FIG. 1.

The individual constituents of the mask pattern inspection apparatus illustrated in FIG. 1 and FIG. 2 represent functional blocks, rather than constituents on the hardware basis. The individual constituents of the mask pattern inspection apparatus are embodied by arbitrary combination of hardware and software, wherein the hardware include a CPU of an arbitrary computer, a memory, a program loaded on the memory so as to embody functions of the constituents illustrated in the drawing, a storage unit such as hard disk for storing the program, and an interface for networking. Modes of embodiment and the apparatus allow various modifications.

FIGS. 3A and 3B illustrate patterns expressed by an identical pattern data, extracted from two chips on the multi-layered-film mask M. For example, FIG. 3A corresponds to the first data to be stored into the pattern memory 20 after the mask inspection starts, and therefore illustrates a pattern in a specific area in a certain chip. FIG. 3B illustrates a pattern in the same area with that illustrated in FIG. 3A, in the chip in adjacent to the chip illustrated in FIG. 3A.

As illustrated in FIG. 3A and FIG. 3B, for the case where a plurality of chips are arranged on the same mask, even the identical pattern in the chips are differently biased depending on location of the chips on the mask.

More specifically, an original pattern 30 illustrated in FIG. 3A is transformed into FIG. 31 by outwardly moving the pattern edges by bias C1 (expanded by an hatched area illustrated in FIG. 3A and FIG. 6), and an pattern 32 in FIG. 3B, which should have the same geometry with the pattern 30, is transformed into FIG. 33 by outwardly moving the pattern edges by bias C2 (expanded by an hatched area illustrated in FIG. 3B and FIG. 6).

Since necessary biases C1, C2 are different depending on location on the mask as described in the above, so that, as illustrated in FIG. 4, a pattern area 34 of the multi-layered-film mask M is divided into a plurality of sub-areas, and the correction data, or bias (Am,n), is determined for each of the sub-areas. A set of correction data is then input, as a flare map, into the inspection apparatus.

The set of data is the data stored in the flare map storage block 26 illustrated in FIG. 1. Boundary lines 35 bounding the areas illustrated in FIG. 4 generally draw different contours depending on density and geometry of the mask pattern, or on the light exposure apparatus to be adopted. Size of the area representing therein a constant bias may not necessarily be constant, and may be different from each other.

Anyway, the flare map is preferably configured so as to correlate a coordinate of a target pattern, or a coordinate of a part of consecutive patterns, with bias. The data is not so complicated as compared with pattern data of semiconductor integrated circuit, and therefore does not always necessarily have a hierarchical structure, but may simply have a flat structure.

Next, methods of collecting and comparing inspection images of the mask pattern will be explained referring to FIG. 5, FIG. 6, and FIGS. 7A and 7B.

First, as illustrated in FIG. 5, a pattern on the multi-layered-film mask M is typically divided into inspection stripes 42, each of which serves as an oblong stripe-form inspection area having a width of 200 μm or around. Next, the mask stage 11 is moved so that the inspection stripe 42 is scanned, and so that magnified inspection images of the pattern contained in the inspection stripe 42 are consecutively captured into the sensor 18, in a form of distribution of detected values by a plurality of pixels 41.

The sensor 18 adoptable herein may be exemplified by a Time Delay Integration (TDI) sensor typically having a horizontal resolution of 2048 pixels and a vertical resolution of 512 stages. The TDI sensor generates an output by transferring charge stage-by-stage in the direction indicated by an arrow 40 in synchronization with feeding motion of the mask stage, while accumulating the charge multiplied by the number of stages. The width of the stripe and the number of pixels of the sensor are not limited to the values described in the above.

FIG. 6 is an explanatory drawing illustrating two patterns illustrated in FIGS. 3A and 3B, which are contained in the different chips but have the same geometry on the design basis, captured by the sensor 18.

In FIG. 6, dotted lines 43 in the vertical direction represent boundary lines of the pixels in the direction of charge accumulation (that is, the direction of scanning of the pattern) of the TDI sensor, and the dotted lines 44 in the horizontal direction represent boundary lines of the pixels in the widthwise direction of the TDI sensor.

Now, an exemplary method of comparing images taken place in the comparison block 23 will be explained, referring to FIGS. 7A and 7B. FIGS. 7A and 7B illustrate an exemplary case where specific pixel arrays are extracted, and images produced by the extracted pixel arrays are compared using an appropriate algorithm.

FIGS. 7A and 7B schematically illustrate light intensity distribution of the inspection image around the pattern and pixel intensity of a single pixel array which is extracted along line B-B' from the inspection image illustrated in FIG. 6. In FIG. 7A, a curve 45 represents a light intensity distribution of the inspection image around the absorber pattern having the amount of correction of flare of C1 (width of the left hatched area in FIG. 6).

While the light intensity distribution is expressed by a smooth curve, the inspection image captured into the pixels gives discrete strings of detection signals, since the inspection image captured in the pixels have integrated values of light intensity on the pixel basis. For example, pixel 45-1 and pixel 45-5 have intensity of inspection image representing absence of the absorber pattern, pixel 45-3 has intensity of inspection image ascribable to the absorber, and pixel 45-2 and pixel 45-4 have intermediate values of the both. Based on the thus-captured detection signals (pixel intensities), a bitmap expansion data corresponded to the curve 45 is generated. The bitmap data is used for comparison.

On the other hand, in FIG. 7B, a curve 46 represents a light intensity distribution of the inspection image around the absorber pattern having the amount of correction of flare of C2 (width of the right hatched area in FIG. 6). Since the amount of correction of flare is assumed herein as C2>C1, the curve 46 gives a smaller value than the curve 45 in the vicinity of the pattern edge. The inspection image captured in the sensor pixels gives strings of detection signals which express the difference.

While the patterns would be judged as separate patterns by the conventional die-to-die comparison, the patterns may be judged as identical ones by this embodiment, by carrying out the process below. Since the amounts of correction of flare C1 and C2 are preliminarily loaded for every pattern to be detected, so that, for example, the inspection image illustrated in FIG. 7A may be reproduced from the inspection image illustrated in FIG. 7B, by calculating an inspection image obtainable when the position of the edge of the absorber pattern is inwardly shifted by (C2−C1). Alternatively, two these patterns may be judged as the identical patterns, by shifting the position of the edge of the absorber pattern obtainable from FIG. 7A inwardly by C1, and by shifting the position of the edge of the absorber pattern obtainable from FIG. 7B inwardly by C2.

In fact, inspection signal intensities of pixels 47-1 and 47-2 which correspond to areas around the pattern edges are correctable, if reflectivity of the inspection light in each of the areas having the absorber pattern formed therein and having no absorber pattern formed therein are preliminarily known.

Another adoptable method may be such as preliminarily simulating an projected image using the mask pattern, preparing a table which depicts changes in the luminous energy to be accumulated in a single pixel as a result of shifting of the pattern edge by the simulation of the projected image, and appropriately making reference to the table. The changes in the light intensity of the pixel may more readily be calculated, if the position of the pattern edge falls on the center portion of the sensor pixel. On the other hand, for the case where the position of the pattern edge falls in the vicinity of the boundary of pixels, ratio of area having the absorber formed therein and area having no absorber formed therein is predicted based on the light intensity, for each of a plurality of adjacent pixels. The pixel intensity may be calculated, by correcting the ratio of area based on the shift (C2−C1) of the position of the pattern edge.

By the process described in the above, a curve 47 which expresses a new light intensity distribution is generated typically in a form of bitmap expanded data, based on the curve 46 which represents the light intensity distribution of the inspection image illustrated in FIG. 7B. The curve 47 is then compared with the bitmap expanded data which represents the light intensity distribution of the inspection image illustrated in FIG. 7A. If there is no pattern defect, the thus-compared light intensity distributions show very good agreement.

Although the shift (C2−C1) of the position of the edge is supposedly smaller than the defect to be detected, the defect may occasionally become smaller as a result of inward shifting of the position of the edge.

In this case, it may be successful, for example, to compare the inspection image obtained from FIG. 7A, after outwardly shifting the position of the edge thereof by (C2−C1), with the inspection image obtained from FIG. 7B. The defect to be detected may, however, still occasionally be processed to give a smaller value, also as a result of outward shifting of the position of the edge. It is, therefore, preferable to carry out both types of calculation, when (C2−C1) exceeds a certain level.

FIG. 8 is a time chart illustrating processing procedures corresponded to a single inspection stripe in the mask pattern defect inspection apparatus of this embodiment.

Figure 14:
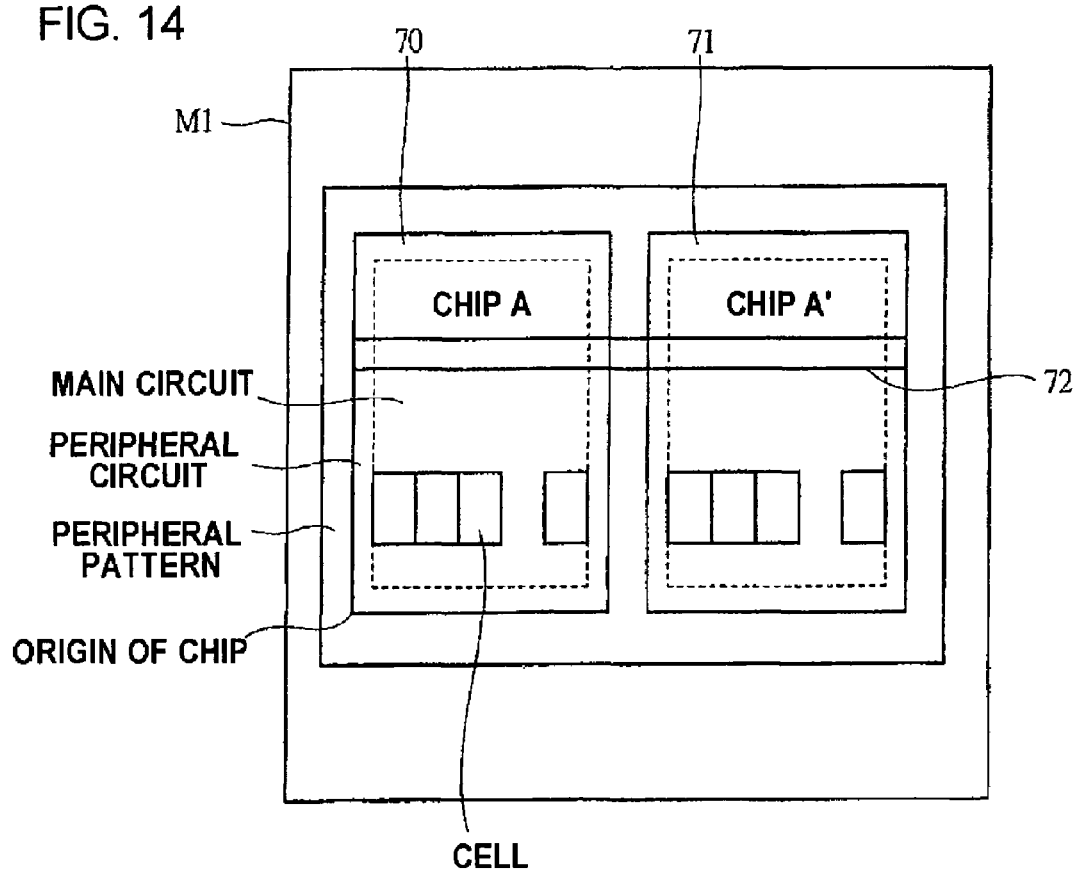
FIG. 14 is a drawing illustrating a relation between a plurality of chips drawn on a mask or a pattern configuration examined by the present inventors, and an inspection stripe.
Figure 15A:
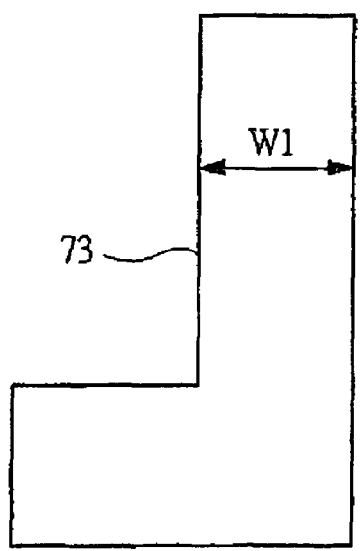
FIGS. 15A and 15B are explanatory drawings illustrating exemplary patterns to be compared with each other examined by the present inventors, having the same geometry on the design basis, but having different dimensions due to difference in position of placement on the mask.
Figure 15B:
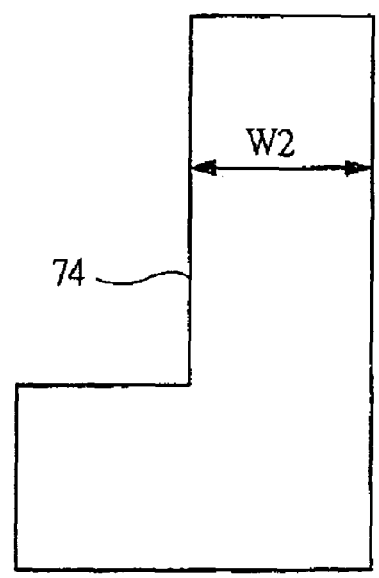

The chip configuration of the mask to be inspected exemplified herein is similar to that illustrated in FIG. 14, in which the chip A (chip 70 in FIG. 14) which serves as a referential chip pattern, and the chip A' (chip 71 in FIG. 14) which serves as a comparative chip pattern, are arranged in the longitudinal direction (X-direction) of the inspection stripe. Scanning of the multi-layered-film mask M is started at time t1, and the sensor 18 is brought into a stand-by mode.

At the same time, data representing the amount of correction of flare of the pattern data to be captured from now on is loaded. The data representing the amount of correction of flare is occasionally loaded also thereafter. When the pixels of the sensor 18 come to reach the chip A at time t2, positional relation between the stage and the sensor image is stored, and capturing of the inspection image data of the chip A into the pattern memory 20 starts.

The capturing of the image data of the chip A completes at time t3. When the pixels of the sensor 18 come to reach the chip A' at time t4, positional relation between the stage and the sensor image is stored, and capturing of the inspection image data of the chip A' starts.

In the period between time t4 and time t5, die-to-die comparison making use of the above-described image processing takes place. In the comparison process, the data representing the amount of correction of flare is occasionally loaded. In the process of die-to-die comparison, the pattern data of the chip A' is input to the comparison block 23. In parallel therewith, the pattern data are sequentially read out from the pattern memory 20, so as to be started from a memory address corresponded to the preliminarily-stored boundary of the chip A, and then input to the comparison block 23.

The comparison block 23 compares two sets of data based on an appropriate algorithm, and judges whether defect exists or not. If two sets of data do not agree, the defect is judged.

For the case where three chips (chip A, chip A', chip A") are arranged in the X-direction, defect is judged by re-loading the measured pattern data of the first chip A from the pattern memory 20 when the third chip A" which serves as the comparative chip pattern is captured, and by inputting the measured pattern data of the chip A" to the comparison block 23 in parallel therewith.

The same will apply also to the case where four or more chips are arranged in the X-direction. Upon completion of capturing of a plurality of chips in a single stripe, the process is temporarily held until the comparison by the comparison block 23 completes, then advances to capturing of the inspection images in the next stripe, and terminates the inspection upon completion of processing of all of the predetermined stripes on the mask.

When the chips repetitively arranged in the width-wise direction (Y-direction) of the inspection stripe are compared with each other, modes of overlapping of the pixels are matched by adjusting the position (Y-coordinate) of the inspection stripe based on the Y-coordinate of the origin of the individual chips.

A flow which collectively describes the above-described capturing of inspection images and comparison process is illustrated in FIG. 9.

First, the first inspection stripe is designated in an area to be inspected on the multi-layered-film mask M, and the capturing of the inspection images is initiated so as to make the multi-layered-film mask M scanned under consecutive movement of the mask stage 11 (step S101). When pixels of the sensor 18 come to overlap the area of the chip A, the inspection image data of the chip A is captured by the sensor 18, and at the same time the data representing the amount of correction of flare corresponded to the chip A is appropriately loaded from the map storage block 26 (step S102). The data representing the amount of correction of flare is determined corresponding to areas on the mask, and therefore do not always have a single value in a single chip.

At the same time, the inspection image is captured into the pattern memory 20 (step S103). When the pixels of the sensor 18 come to overlap the chip A' under consecutive movement of the mask stage 11, the inspection image of the chip A' is captured, and the data representing the amount of correction of flare corresponded to the chip A' is appropriately loaded from the flare map storage block 26 as the amount of shifting of the edge of the contour of the pattern.

At the same time, these data, and the pattern data of the chip A read out from the pattern memory 20 are input to the comparison block 23 (step S104). In the comparison block 23, the images of two chips are compared using the above-described algorithm, to thereby judge whether defect is found or not (step S105). If any defect was found, defect information is displayed or recorded depending on needs.

Whether three or more chips are contained in a single stripe or not is then judged (step S106), and if contained, the third and succeeding chips are subjected to similar processes of comparison and judgment of defect (step S107).

Upon completion of process made over the entire range of a single stripe, whether the inspection of defect in a predetermined area on the mask was completed or not is judged (step S108). If uncompleted, a new inspection stripe is designated (step S109), the multi-layered-film mask M is positioned at the start position of the next stripe by re-positioning the mask stage 11, and the procedure returns back to step S101 to repeat the comparative inspection. Upon completion of processes over all stripes in the predetermined area on the mask, the defect inspection terminates.

In the above-described embodiment, DUV light was exemplified as the inspection light for illuminating the multi-layered-film mask M. The die-to-die comparison may alternatively be proceeded in a fully similar manner, by irradiating electron beam onto the multi-layered-film mask M, and by using an electron detector, which is composed of a scintillator combined with a photo-multiplier, as the sensor.

The above-described embodiment explained inspection of a reflective mask. The die-to-die comparison after shifting of the edge position of the inspection image may, or course, be adoptable also to a transmission mask.

In conclusion, according to the first embodiment, in the process of inspection of pattern defect of a mask, having a plurality of chips having the same pattern repetitively drawn therein, the pattern may be inspected according to a method similar to the conventional die-to-die comparison, even if different kinds of flare correction are provided on the chip basis, or depending on locations in the chips, by taking geometrical difference in the flare correction into consideration.

Second Embodiment

Figure 10:
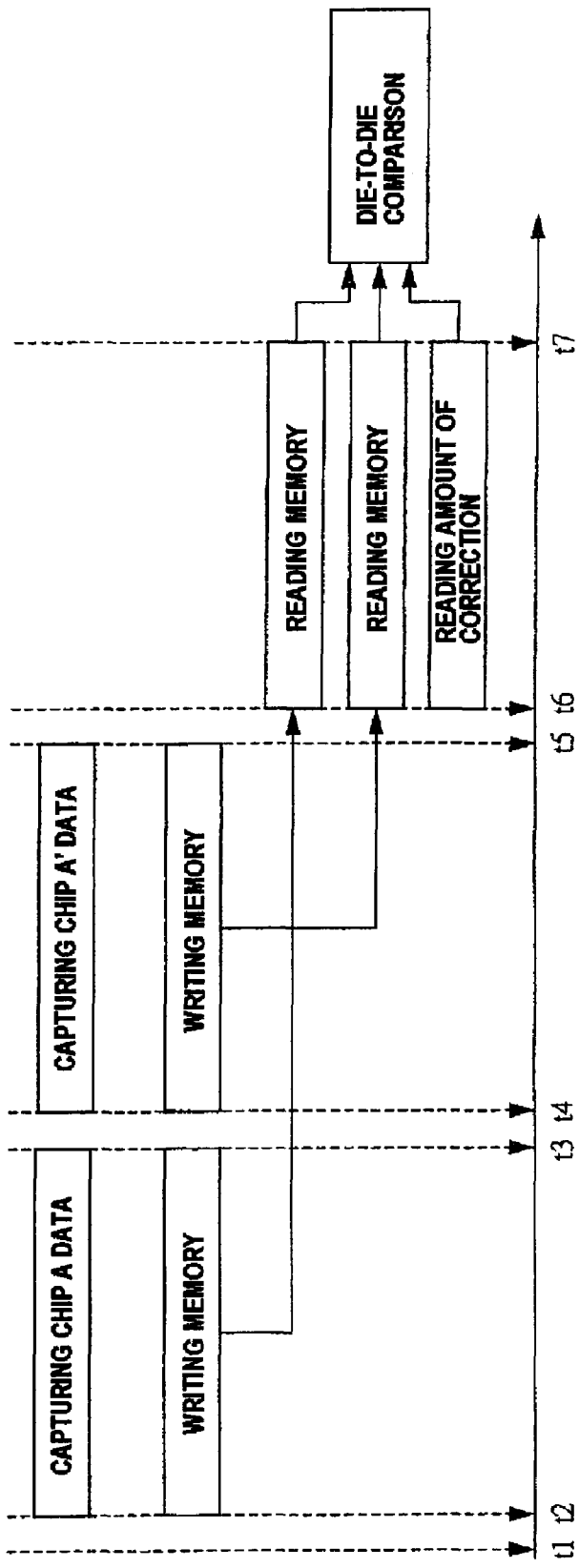
FIG. 10 is a time chart illustrating processing procedures of the inspection images corresponded to a single inspection stripe according to a second embodiment of the present invention.

FIG. 10 is a time chart illustrating processing procedures of the inspection images corresponded to a single inspection stripe according to a second embodiment of the present invention.

In the second embodiment, a method of inspection for the case where the process of comparing and judging the images having the amount of correction of flare incorporated therein takes longer time than that of the process of capturing the inspection images. This is understood as the case where the above-described first embodiment may cause timing error because the process of comparison cannot catch up with the process of capturing.

In the second embodiment, the pattern memory 20 (FIG. 1) has a capacity sufficient for storing measured image data of all chips over the full length of the strip. Even if the process is in the midst of the inspection based on the image comparison in the stripe, and in the midst of the storing the pattern, the configuration allows parallel execution of a writing operation of newly-captured inspection image data and a reading operation of preliminarily-stored measured pattern data. The configuration also allows reading operation of the preliminarily-stored measured pattern data of a chip, prior to the currently-captured chip, in the same inspection stripe.

In this configuration, storage of the measured pattern data into the pattern memory 20 begins at first chip A, which is at the head of the inspection stripe. Next, at the same time the measured pattern data of the image of the second chip A' starts to be stored into the pattern memory 20, the inspection image data of the chip A and the measured image data of the chip A' are read out from the pattern memory 20 in a parallel manner, and then sent to the comparison block 23 again in a parallel manner, so as to allow the defect judgment to proceed.

The reading-out from the pattern memory 20 herein proceeds while being governed by the progress of the process of comparison and judgment in the comparison block 23.

Accordingly, even if the rate of process of comparison and judgment in the comparison block 23 is slower than the rate of capturing of the inspection image of the chip, storage and comparison of the measured pattern data can proceed, while allowing the write-in operation into the pattern memory 20 to precede.

Even if the comparison of the images of the chip A and the chip A' in the comparison block 23 remains unfinished when the capturing of the image of the chip A' completes, the mask stage keeps on moving so as to continue capturing of the images of the third and succeeding chips.

The process of comparison and judgment in the comparison block 23 proceeds in a chasing manner. When the capturing of images of a plurality of chips in a single stripe completes, completion of the process of comparison and judgment in the comparison block 23 is waited, and upon completion of the process, the next striped is inspected.

Another possible method may be such as illustrated in FIG. 10, in which data over the full length of a single inspection stripe and the appropriately corresponded data of the amount of correction of flare are fetched, the measured data is then read out from the pattern memory 20, and thereafter the comparison of the inspection images and the defect judgment are carried out.

As has been described in the above, according to the second embodiment, the pattern may be inspected based on the die-to-die comparison method without causing timing error, even for the case where the process of comparing and judging the images having the amount of correction of flare incorporated therein takes longer time than that of the process of capturing the inspection images.

Third Embodiment

Figure 11:
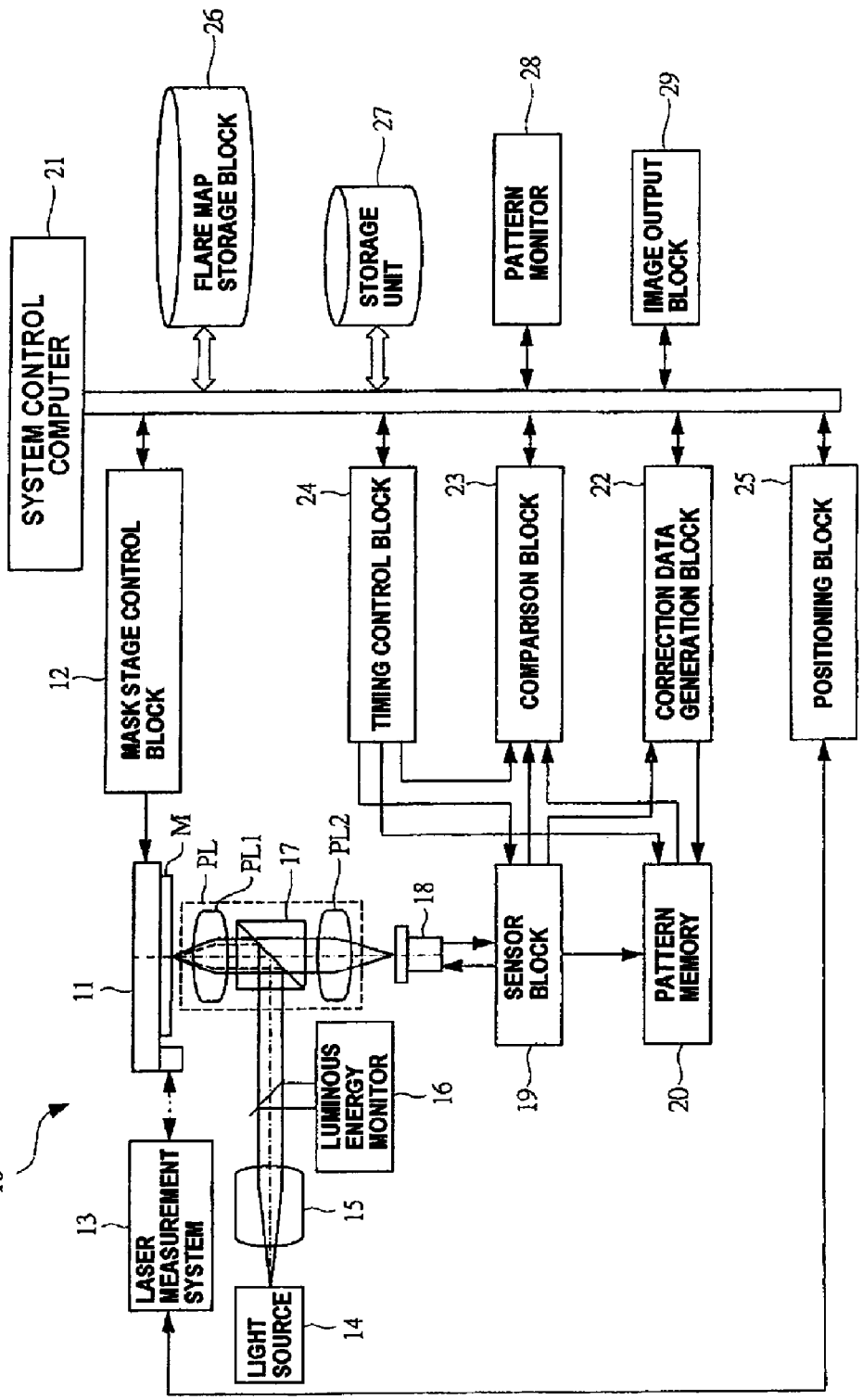
FIG. 11 is an explanatory drawing illustrating an exemplary configuration of a mask pattern defect inspection apparatus according to a third embodiment of the present invention.
Figure 12A:
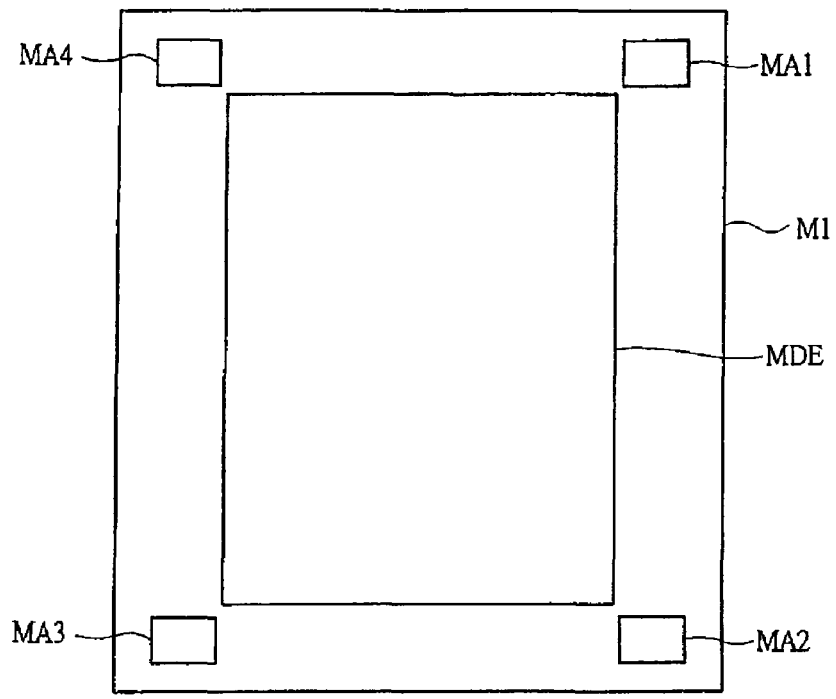
FIGS. 12A and 12B are explanatory drawings illustrating an exemplary configuration of an EUVL mask examined by the present inventors.
Figure 12B:
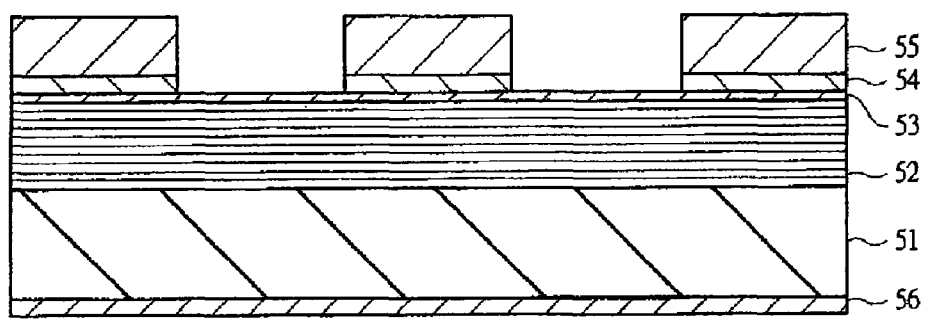
Figure 13:
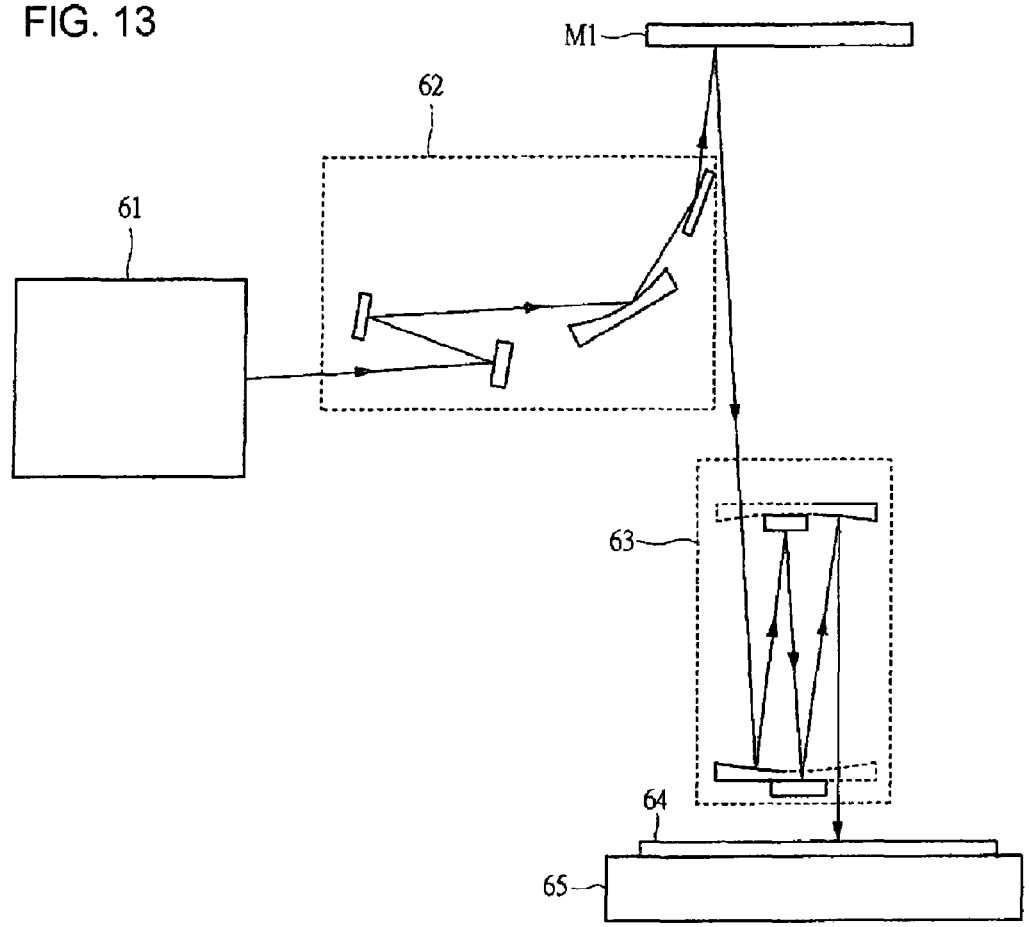
FIG. 13 is a drawing schematically illustrating an EUV projection exposure apparatus used for transferring an EUVL mask pattern, examined by the present inventors, onto a semiconductor substrate.

FIG. 11 is an explanatory drawing illustrating an exemplary configuration of a mask pattern inspection apparatus according to a third embodiment of the present invention.

The third embodiment will explain an exemplary case where a predictive value of the inspection image is preliminarily calculated by subtracting influence of the flare correction data C1, before the inspection image of the first chip A is stored into the pattern memory 20.

Since the predictive value corresponds to an inspection image obtainable when there is no flare correction data, so that the process of subtraction of the influence of the correction data may be omissible if the amount of correction of flare with respect to the pattern of the chip A is zero.

Configuration of the inspection apparatus of this embodiment is similar to that of the apparatus explained in the first embodiment (FIG. 1), except that the inspection image data of the chip obtained by the sensor block 19 in this embodiment is once sent to the correction data generation block 22, and then stored into the pattern memory 20 after being processed by the above-descried calculation.

In the process over a single inspection stripe, the inspection image data of the chip A, having the amount of correction of flare corresponded to zero, is stored into the pattern memory 20, and the inspection image data of the second chip A' is captured.

The data is input into the comparison block 23. In parallel therewith, the pattern data of the chip A, which are preliminarily recorded as the inspection images having the amount of correction of flare corresponded to zero, are sequentially read out from the pattern memory 20, and input to the comparison block 23.

The comparison block 23 carries out the defect judgment by comparing two sets of data, wherein with respect to the inspection image of the chip A', a corresponding amount of correction of flare C2 is read out at the correction data generation block 22. An inspection image obtainable by shifting the edge position of the absorber pattern by C2 is then calculated, and the calculated image and the corrected inspection image of the first chip A are compared.

Accordingly, both of the inspection images actually compared herein may be equivalent to those of design pattern subtracted by the flare correction data. Two sets of measured pattern data are compared by such process of comparison and an appropriate algorithm, and defect is judged if the both do not agree.

Another possible embodiment may be such as capturing, not only for the first chip A, but also for the second and succeeding chips, the inspection images of the individual patterns are fetched. If the corresponding data which represent the amount of correction of flare are not zero, the inspection images are then sent to the correction data generation block 22, subtracted by influence of the correction data which represents the amount of correction of flare, sequentially stored into the pattern memory 20, and, after completion of collection of the inspection image data in the stripe, the corrected inspection images of the chips A and A' are read out onto the comparison block 23 and compared.

As has been described in the above, according to the third embodiment, the inspection images, even if applied with different amounts of correction of flare depending on the areas, may be compared by die-to-die comparison, after being relieved from any influences of the amount of correction of flare, so that stable inspection may be ensured.

The present invention accomplished by the present inventors have been explained referring to the specific embodiments. The present invention is, however, by no means limited to the above-described embodiments, and of course allows various modifications without departing from the spirit of the present invention.

It is apparent that the present invention is not limited to the above embodiments, but may be modified and changed without departing from the scope and spirit of the invention.

What is claimed is:

1. A method of inspecting a mask pattern for judging presence of pattern defect in a plurality of chip patterns formed on an EUV lithographic mask, said method comprising:

acquiring a referential measurement pattern by irradiating light or electron beam onto a referential chip pattern contained in a referential inspection area, which is selected as a reference for comparison out of said plurality of chip patterns, and by capturing reflected light, secondary electron or reflected electron from said referential inspection area using an imaging unit;

acquiring a comparative measurement pattern by irradiating light or electron beam onto a comparative chip pattern contained in a comparative inspection area, which is selected from the plurality of chip patterns but other than said referential chip pattern, and by capturing reflected light, secondary electron or reflected electron from said comparative inspection area using an imaging unit;

detecting positions of the acquired referential measurement pattern and the acquired comparative measurement pattern;

correcting said referential measurement pattern and said comparative measurement pattern, based on at least one of first correction data for correcting said referential measurement pattern and second correction data for correcting said comparative measurement pattern, loaded from a flare map storage block which stores flare correction data used for correcting an influence of flare possibly generated in EUV lithography for each area in a mask pattern, the first correction data corresponding to the position of the referential measurement pattern, the second correction data corresponding to the position of the comparative measurement pattern; and judging presence of pattern defect by comparing the thus-corrected referential measurement pattern and the thus-corrected comparative measurement pattern.

2. The method of inspecting a mask pattern as claimed in claim 1, wherein said correcting of said referential measurement pattern and said comparative measurement pattern further comprises:

storing said referential measurement pattern into a pattern memory;

storing said comparative measurement pattern into said pattern memory;

correcting said referential measurement pattern, stored into said pattern memory, based on said first correction data; and correcting said comparative measurement pattern, stored into said pattern memory, based on said second correction data.

3. The method of inspecting a mask pattern as claimed in claim 1, wherein said correcting said referential measurement pattern and said comparative measurement pattern further comprises:

storing said acquired referential measurement pattern into a pattern memory;

correcting said referential measurement pattern, stored into said pattern memory, based on said first correction data; and correcting the thus-acquired comparative measurement pattern based on said second correction data.

4. The method of inspecting a mask pattern as claimed in claim 1, wherein said correction data is data for correcting an influence of flare possibly generated in EUV lithography.

5. The method of inspecting a mask pattern as claimed in claim 4, wherein said mask pattern is divided into a plurality of sub-areas, each of said plurality of sub-areas has correction data preliminarily determined, and said correction data corresponded to said sub-area containing said referential inspection area is used as said first correction data, and said correction data corresponded to said sub-area containing said comparative inspection area is used as said second correction data.

6. The method of inspecting a mask pattern as claimed in claim 5, wherein said correction data is preliminarily determined with respect to each mask pattern.

7. The method of inspecting a mask pattern as claimed in claim 1, wherein said EUV lithographic mask is a multi-layered-film mask.

8. The method of inspecting a mask pattern as claimed in claim 1, wherein said referential chip pattern is a chip pattern formed closest to a corner of said EUV lithographic mask.

9. The method of inspecting a mask pattern as claimed in claim 1, wherein the center wavelength of exposure irradiated on said EUV lithographic mask is 13.5 nm.

10. A mask pattern inspection apparatus for judging presence of pattern defect in a plurality of chip patterns formed on an EUV lithographic mask, said apparatus comprising:

a pattern detection block which respectively acquires a referential measurement pattern and a comparative measurement pattern, by detecting reflected light, secondary electron or reflected electron respectively from an arbitrary inspection area in a referential chip pattern, and in a comparative chip pattern other than said referential chip pattern, out of said plurality of chip patterns;

a position detection block which respectively detects positions of the thus-detected referential measurement pattern and the thus-detected comparative measurement pattern;

a flare map storage block which stores flare correction data used for correcting influence of flare possibly generated in EUV lithography for each area in a mask pattern; and a comparison block which judges presence of pattern defect, by acquiring a first flare correction data which corresponds to the position of said referential measurement pattern, and a second flare correction data which corresponds to the position of said comparative measurement pattern from said flare map storage block, by correcting said referential measurement pattern using said first flare correction data, by correcting said comparative measurement pattern using said second flare correction data, and by comparing the thus-corrected referential measurement pattern and the thus-corrected comparative measurement pattern.

11. The mask pattern inspection apparatus as claimed in claim 10, further comprising a pattern memory which stores the thus-detected referential measurement pattern, and the thus-detected comparative measurement pattern, wherein said comparison block uses said referential measurement pattern and said comparative measurement pattern thus stored in said pattern memory.

12. The mask pattern inspection apparatus as claimed in claim 10, further comprising a pattern memory which stores the thus-detected referential measurement pattern, wherein said comparison block acquires said referential measurement pattern from said pattern memory, and acquires said comparative measurement pattern from said pattern detection block.

13. The mask pattern inspection apparatus as claimed in claim 10, wherein said EUV lithographic mask is a multi-layered film mask.

14. The method of inspecting a mask pattern as claimed in claim 4, wherein the first correction data is data for correcting the influence of flare corresponding to the referential chip pattern, and the second correction data is data for correcting the influence of flare corresponding to the comparative chip pattern.

15. The method of inspecting a mask pattern as claimed in claim 1, wherein the referential measurement pattern is corrected based on the first correction data for correcting the referential measurement pattern, loaded from elsewhere.

16. The method of inspecting a mask pattern as claimed in claim 1, wherein the comparative measurement pattern is corrected based on the second correction data for correcting the comparative measurement pattern, loaded from elsewhere.

* * * * *